(12) United States Patent
Guilford et al.

(10) Patent No.: US 8,114,913 B1
(45) Date of Patent: Feb. 14, 2012

(54) SYSTEMIC ADMINISTRATION OF NAC AS AN ADJUNCT IN THE TREATMENT OF BIOTERROR EXPOSURES SUCH AS SMALLPOX AND USE IN COMBINATION WITH DHEA FOR THE TREATMENT OF SMALLPOX

(75) Inventors: F. Timothy Guilford, Palo Alto, CA (US); Brooke Schumm, III, Ellicott City, MD (US)

(73) Assignee: Your Energy Systems, LLC, Palo Alto, CA (US)

( * ) Notice: Subject to any disclaimer, the term of this patent is extended or adjusted under 35 U.S.C. 154(b) by 18 days.

(21) Appl. No.: 12/486,851

(22) Filed: Jun. 18, 2009

Related U.S. Application Data

(62) Division of application No. 10/289,934, filed on Nov. 7, 2002.

(60) Provisional application No. 60/371,590, filed on Apr. 11, 2002, provisional application No. 60/338,267, filed on Nov. 9, 2001.

(51) Int. Cl.
*A01N 33/08* (2006.01)
*A61K 31/33* (2006.01)

(52) U.S. Cl. ............................................. 514/665
(58) Field of Classification Search .............. None
See application file for complete search history.

(56) References Cited

U.S. PATENT DOCUMENTS
5,837,269 A * 11/1998 Daynes et al. ............. 424/278.1

FOREIGN PATENT DOCUMENTS
EP    1046399    * 10/2000

* cited by examiner

*Primary Examiner* — Alton Pryor
(74) *Attorney, Agent, or Firm* — Brooke Schumm III; Daneker, McIntire, Schumm et al

(57) ABSTRACT

The invention is for the combination and related methods of N-acetyl-cysteine oral, inhaled, or intravenous, or glutathione inhaled or intravenous, generally in combination with antibiotic and/or antiviral therapy to ameliorate the toxic effects of infection with materials used in Bioterror incidents such as *Bacillus anthracis* and smallpox virus, and alternatively, upon exposure to radiation, during testing, and vaccination, as treatment prior to treatment with antibiotic or antiviral therapy to ameliorate the toxic effects of infection and exposure with these organisms.

3 Claims, No Drawings

SYSTEMIC ADMINISTRATION OF NAC AS AN ADJUNCT IN THE TREATMENT OF BIOTERROR EXPOSURES SUCH AS SMALLPOX AND USE IN COMBINATION WITH DHEA FOR THE TREATMENT OF SMALLPOX

CONTINUATION DATA

This application is a divisional application of pending U.S. application Ser. No. 10/289,934 filed Nov. 7, 2002 entitled "Systemic Administration Of NAC As An Adjunct In The Treatment Of Bioterror Exposures Such As Anthrax, Smallpox Or Radiation And For Vaccination Prophylaxis, And Use In Combination With DI LEA For The Treatment Of Smallpox And Other Viruses" which in turn claims benefit of provisional application 60/338,267 filed on Nov. 9, 2001 entitled "Systemic Administration Of Glutathione Or Precursor Such As NAC As An Adjunct In The Treatment Of *Bacillus Anthracis* Exposure Or Infection, and of provisional application 60/371,590 filed on Apr. 11, 2002 entitled Use Of Glutathione Precursor In The Treatment Of Smallpox And The Use Of Glutathione Precursor In The Treatment Of Radiation Exposure, The Use Of The Combination Of Glutathione Precursor And DHEA For The Treatment Of Smallpox And Other Viruses," all of which are incorporated by reference herein.

SUMMARY

The invention is for the combination of N-acetyl-cysteine oral, inhaled, or intravenous, or glutathione inhaled or intravenous, and antibiotic and/or antiviral therapy to ameliorate the toxic effects of infection with materials used in Bioterror incidents such as *Bacillus anthracis* and smallpox virus, and alternatively, upon radiation exposure, during testing or vaccination, as treatment prior to treatment with antibiotic or antiviral therapy to ameliorate the toxic effects of infection and exposure with these organisms.

TECHNICAL FIELD

The present invention relates to the treatment of infection with *Bacillus anthracis* or smallpox virus using systemic antioxidant support in forms including intravenous NAC and inhaled glutathione individually and in combination and as an adjunct therapy with antibiotic and/or antiviral agents. Systemic antioxidant support using intravenous NAC and inhaled glutathione individually and in combination is also used as therapy for ameliorating the effects of radiation induced depletion of antioxidant defense. Prophylactic protection against complications after smallpox vaccination and radiation exposure is discussed. Combination with DHEA for the same purposes is presented.

BACKGROUND OF THE INVENTION

Bioterror exposures include the possibility of exposure to either individual or combinations of biologic and radiation agents. After a documented or suspected Bioterror exposure, there is a variable period of time during which it is not clear what agent was used or what therapy would be most specific. In this situation it may not be known what specific therapy may be most effective, such as an antiviral or antibiotic. During this period and regardless of what specific agent is chosen, antioxidant support in the form described in this invention may be useful to support the immune system and improve the likelihood of survival of the affected individual.

The biology with the bacteria *Bacillus anthracis* and smallpox Smallpox virus, variola are reviewed as background for the invention.

In the early stage of exposure to anthrax the bacteria is usually in the spore form. The body uses the macrophage to phagocytize the spore and it is carried to regional lymph nodes. The formation of vegetative organisms thus occurs in the lymphatic system and spreads to the bloodstream. In a small number of cases, systemic anthrax can lead to meningeal involvement by means of lymphatic or hematogenous spread. At autopsy a classic finding of anthrax infection is the finding of extensive hemorrhage of the leptomeninges, which gives them a dark red appearance described as "cardinal's cap."

In cases of pulmonary anthrax, peribronchial hemorrhagic lymphadenitis blocks pulmonary lymphatic drainage, leading to pulmonary edema. Death results from septicemia, toxemia, or pulmonary complications and can occur one to seven days after exposure.

Illness and death related to infection with the bacteria *Bacillus anthracis* is mediated by the interaction of three toxins formed by anthrax. The first is an antiphagocytic capsule (poly-n-glutamic acid), edema toxin and lethal toxin. The antiphagocytic factor inhibits phagocytosis and locks onto the scavenging cell called macrophage. This is followed by the insertion of the two other toxins, lethal factor toxin and edema toxin. The lethal factor appears to mediate the rapid onset of shock and death associated with systemic anthrax. While edema toxin causes swelling in all cells, lethal toxin exerts its effect selectively on the macrophage, even though the lethal toxin is injected into all cells (Hanna P et al, "On the Role of Macrophages in Anthrax," Proc Natl Acad Sci (PNAS) USA: Vol. 90; 10198-10201, 1993).

The presence of low levels of toxin in macrophages stimulates the production of cell signaling hormones called cytokines such as IL-1 and TNF. At low levels these cytokines stimulate the immune response of the host, but at higher levels they mediate damage to the host, even extending to fatal shock (Hanna P et al, "On the Role of Macrophages in Anthrax," PNAS USA: Vol. 90; 10198-10201, 1993). It is postulated that the macrophage accumulates the IL-1 until a critical level of toxin is reached which causes lysis of the cell and uncontrolled release of the accumulated IL-1 in a large amount that can lead to shock and death. The accumulation of IL-1 in many macrophages coupled with the contemporaneous release from many cells can result in death being the presenting symptom of anthrax infection (Hanna Pet al, PNAS USA: Vol. 90; 10198-10201, 1993).

Thus the macrophage plays a contradictory role. With most infections the macrophage plays a protective role ingesting and incapacitating invading organisms. With anthrax the normal protective mechanism has been mal-appropriated to facilitate the lethality of the anthrax toxin. The macrophage becomes the mediator of the lethality related to the toxin.

Macrophage disruption is mediated by an increase in the formation of Reactive Oxygen Species also known as Free Radicals. At high levels the toxins cause destruction of the macrophages. At lower levels the toxin-mediated free radicals stimulates these cells to produce cytokines (interleukin-1 beta and tumor necrosis factor-alpha), which induce systemic shock and death. Antioxidants have been shown to moderately inhibit anthrax toxin-induced cytokine production in vitro. NAC also blocked the production of TNF-alpha in rat peritoneal macrophages activated with endotoxin (Pahan K, "N-acetyl cysteine inhibits induction of NO production by endotoxin or cytokine stimulated rat peritoneal macrophages C6 glial cells and astrocytes," Free Radic Biol Med, 24(1):

39-48 1998 Jan. 1). Mice pretreated with N-acetyl-L-cysteine showed partial protection against anthrax toxin exposure (Hanna P et al, "Role of macrophage oxidative burst in the action of anthrax lethal toxin," Molecular Medicine (Mol Med) 1994 November; 1 (1):7-18).

Increasing the level of cysteine, a precursor of glutathione reduces the production of the cytokines and TNF-α that caused the body more harm than benefit. The increase in glutathione precursor also increases the potential for surviving toxin exposure in animals (Hanna P et al, "Role of macrophage oxidative burst in the action of anthrax lethal toxin," Mol Med 1994 November; 1(1):7-18). Other studies have also demonstrated that reactive oxygen species are involved in the deterioration of cardiac function seen in endotoxin shock and their effect can be diminished by the use of anti-oxidants (Pattanaik U et al, "Reactive oxygen species and endotoxic shock: effect of dimethylthiourea," J Cardiovasc Pharmacol Ther 2001 July; 6(3):273-85). The use of NAC prior to exposure to anthrax or its toxins have already been demonstrated to help reduce the negative effects of ROS and the release of cytokines in cell studies. NAC prior to exposure reduces the lethality of anthrax in animal studies.

While Hanna et al suggest positive effect in mice by NAC on exposure to toxins and on survivability of macrophages in culture," (Hanna P et al, "Role of macrophage oxidative burst in the action of anthrax lethal toxin," Mol Med 1994 November; 1(1):7-18), no reference cites a method or combination of NAC with antibiotics to treat anthrax in humans or mammals. Dixon, Meselson, Guillemin and Hanna, "Anthrax," N. Engl. J. Med. 341(11): 815-26, Sep. 9, 1999 specifically note "Unfortunately, anti-toxin preparations are not currently available in the United States. Based on the findings of the animal and cell studies, glutathione and glutathione precursors containing cysteine or its physiologic form cystine represent a potent strategy for ameliorating the effects of inhalation anthrax.

Viruses are strands of information, either RNA or DNA, that depend on living cells to provide either the additional components or an environment which allow the virus to reproduce. Since they neither breathe nor reproduce on their own they are not considered living. After using the host cell machinery and enzymes to make new copies of itself, viruses program the production of a new covering which allow it to be released out of the cell and accepted by the next cell. To accomplish replication most viruses need to use the information contained in the DNA of the cell. Smallpox viruses are unusual in that they contain all of the information that they need to replicate, however it still needs the interior of the cell to replicate. Scientists who study the evolution of viruses conjecture that the information in the smallpox virus may have belonged to another organism that has now become incorporated in the DNA replication machinery of our cells (Takemura M, "Poxviruses and the origin of the eukaryotic nucleus," J Mol Evol. Vol. 52(5):419-25, May 2001.). Viruses cause problems by changing the machinery of the cell that it has commandeered and by creating so many copies of itself that the cell cannot maintain its normal function, ceases functioning normally and may even rupture, releasing large amounts of virus.

Smallpox virus, called variola, is a DNA virus containing all the information that is necessary to reproduce; however it must be incorporated into a cell for reproduction to occur. This allows for the virus to replicate in the cytoplasm of a cell and to utilize the cell wall machinery to form a capsule and be released rapidly. The virus, after replicating in various tissue cells and creating a large number of copies, is released into the bloodstream before invading the skin and, in most cases, developing the skin lesions, or pocks that give rise to the common name for the disease state triggered by the virus: smallpox. While this is happening, the patient may not feel ill. Usually 12 days after exposure a feverish illness appears. Two to three days later the characteristic skin rash may appear. The rash appears as small pink spots called macules and progresses to enlarged, slightly raised papules. The papules progress to blisters. Eventually the blisters become turbid, looking like pustules, which were previously called pocks and are the characteristic feature for which the virus is named. The pustules then dry up and shrink, leaving a hard crust that eventually flakes off leaving a sunken scar. The distribution of the rash is characteristic of smallpox with the head and extremities affected more than the trunk.

Usually the severity of the disease follows the severity of the rash, but severe illness may precede the rash with the patient becoming prostrate before the outbreak of a rash. It is also possible to spread the virus without developing the rash, which means that outbreaks can be precipitated by individuals without rash or even severe illness.

Mortality: There is no treatment recognized once the illness has started. There are reports of mortality of 30% or more in unvaccinated populations (Henderson D A et al, "Consensus statement regarding Smallpox," J. Am. Med. Assoc. Vol. 281(22):2127-37, Jun. 9, 1999).

Poxviruses have caused infections in man documented as far back as the Egyptian pharaohs. The Pharaoh Ramses V was apparently inflicted with the virus at the time of his death in 1157 B.C. Smallpox inflicted Europe in 710 A.D. Cortez carried smallpox to the America's in 1520 and precipitated the death of 2 million Aztecs in the following 2 years. In the cities of $18^{th}$ century Europe, smallpox reached plague proportions as the highly infectious disease affected rich and poor alike, with five reigning monarchs dieing with the disease (http://www.tulane.edu/~dmsander/WWW/335/Poxviruses.html). The last outbreak of small pox occurred in modern times in Somalia in 1977.

While most pox diseases, such as chickenpox, occur in man as well as animals, only smallpox uses humans as its reservoir. The selectivity of smallpox has allowed the success of an aggressive immunization campaign by the World Health Organization to eradicate the disease. The structure of the poxviruses are similar, which allows the use of a similar, but less virulent virus to effect a cross reacting immunization. In addition, smallpox causes only acute disease and does not set up dormant disease such as the Herpes virus does. The result is that individuals who survive a smallpox infection have immunity that lasts for life.

The fact that the animal poxviruses share similar biochemical characteristics on their covers that are recognized by the immune system allowed Edward Jenner to demonstrate the concept of vaccination in 1796 (Id). It had been observed that the milkmaids, while frequently affected with cowpox, rarely if ever became infected with smallpox. Jenner used cowpox, obtained from a milkmaid to inoculate an 8-year-old boy. Later, Jenner challenged the boy with an inoculation of smallpox and demonstrated that the immunization led to protection from the infection.

Vaccination became common around the world beginning around 1800, but smallpox was not eradicated until the World Health Organization made a major commitment to eradicate the virus with a worldwide vaccination campaign. Vaccination is done with a less virulent virus called vaccinia. The vaccinia virus used in modern vaccinations may have developed through the serial passage from arm to arm since the time of Jenner.

Smallpox causes serious infections with skin lesions and it is spread easily through respiratory contact with cough droplets. As a biological weapon, smallpox represents a serious threat as it has been reported to carry a case-fatality rate of 30% or more in unvaccinated populations. In addition there is no antiviral therapy specific for smallpox (Henderson D A et al, "Consensus statement regarding Smallpox," Jour Amer Med Assoc. Vol. 281(22):2127-37, Jun. 9, 1999). The ability of an unvaccinated individual thus becomes dependent on the capacity of the individuals immune system to respond to the virus.

While smallpox is unique in its ability to replicate in the cytoplasm of a cell, it has common features with other viruses that make it identifiable by the immune system. Apparently the viral covering is different from self-tissue to the extent that an immune response is created to the viral cover. This is the foundation for the use of the vaccinia virus as a vaccine to stimulate antibodies to smallpox. It is the ability of the immune system to process the viral information, produce antibodies and coordinate the immune cell response for removal of virus that makes the immune system an effective protector against viruses.

Enhancing immune cell function with nutrient materials such as N-Acetyl-cysteine, which increase glutathione in the body and inside cells, will increase the immune surveillance and response mechanism and increase the likelihood of surviving a smallpox infection. Further, even for weakened virus, or cross-reacting immunization, N-Acetyl cysteine, which increases glutathione in the body and inside cells, increases and favorably influences immune response and lessens the likelihood of complications from vaccination.

Exposure of cells to virus decreases the intracellular glutathione, starting immediately after virus challenge. In a study with the herpes simplex virus type 1 (HSV-1) the addition of glutathione to the culture was not only able to restore the intracellular glutathione levels to near normal levels, but was also able to inhibit over 99% of the replication of HSV-1 (Palamara A T et al., "Evidence for antiviral activity of glutathione: in vitro inhibition of herpes simplex virus type 1 replication," Antiviral Res, Vol. 27(3):237-53 1995). Additionally, it was observed that the inhibition was concentration dependent and was maintained even if the glutathione was added as late as 24 hours after virus challenge, when the virus was fully established. Studies of the HSV-1 infected cells showed that glutathione dramatically reduced the number of extracellular and intracytoplasmic virus particles. Nucleocapsids were still detected within the nuclei of glutathione treated cells. The decrease in virus replication was related to a decrease in glycoprotein B, which is crucial for the release and infectivity of the virus. This suggests that glutathione inhibits the replication of HSV-1 by interfering with very late stages of the virus life cycle and not by interfering with cellular metabolism Id.

Viral pathogenesis and mutation is increased by free radical mediated oxidation (Akaike T, "Role of free radicals in viral pathogenesis and mutation Review Medical Virology," Vol. 11(487-101, March-April 2001). The mechanism may be related to the depletion of antioxidant with resulting increase in oxidation. The increase in oxidation decreases the available glutathione. The oxidation stress status of the individual has been demonstrated to affect the pathogenicity of virus in animal studies (Beck M A et al, "Host nutritional status and its effect on a viral pathogen," J Infect Disease Vol. 182 Suppl 1:S93-96, September 2000).

It is well documented that cellular immune function, termed T helper cell type 1 (TH1) function, is affected by the level of glutathione. Antigen presenting cells deficient in glutathione predispose to the formation of a TH2 response with a decrease in TH1 or cell mediated immune response (Peterson J D et al, "Glutathione levels in antigen-presenting cells modulate TH1 versus TH2 response pattern," Proc Natl Acad Sci USA, Vol. 95(6):3071-6, Mar. 17, 1998). Cytotoxic T cell function, which is important in the management of viral infection, is decreased by 30% in animals deficient in glutathione (Lawrence B P et al, "Gamma-glutamyltranspeptidase knockout mice as a model for understanding the consequences of diminished glutathione on T cell-dependent immune responses," European Journal Immunology Vol. 30(7):1902-10, July 2000). Thus, maintaining the glutathione level will help maintain a more favorable balance in the immune responses and an increase in survival. NAC has been demonstrated to increase and maintain the intracellular level of glutathione and protect against intracellular oxidative damage (Afaq F et al, "N-acetyl L-cysteine attenuates oxidant-mediated toxicity induced by chrysotile fibers," Toxicology Letters Vol. 117(1-2):53-60, Sep. 30, 2000).

Intravenous NAC will improve survival of individuals infected with the smallpox virus by either of two methods.
1. NAC may contribute to a direct reduction in viral replication
2. NAC improves the immune surveillance and responsiveness of the immune system.

In addition, regardless of exposure, whether it is bacterial or viral, NAC has been shown to be of benefit in the reducing the ventilator time in individuals with sepsis who require respiratory support. Intravenous NAC has been shown in humans with adult respiratory distress syndrome in patients with septic shock to be effective in reducing length of stay in the intensive care unit from 32 days to 13 days (Spapen H et al, "Does N-acetyl-L-cysteine influence cytokine response during early human septic shock?," Chest, Vol. 113(6):1616-24 June, 1998. One of the beneficial mechanisms of NAC demonstrated in the study was the reduction in the production of the interleukin IL-8, a potential mediator of lung injury. Intravenous NAC infusion to lab rats after exposure to endotoxin reduced the features associated with septic shock (Schmidt W et al, Intensive Care Med, Vol. 24(9):967-72 Sep. 1998.

Studies have also demonstrated that reactive oxygen species are involved in the deterioration of cardiac function seen in endotoxin shock and their effect can be diminished by the use of antioxidants (Pattanaik U et al, J "Reactive oxygen species and endotoxic shock: effect of dimethylthiourea". Cardiovascular Pharmacology Therapy., Vol. 6(3):273-85 Jul. 2001.

Thus, Intravenous NAC becomes an important adjunct in the management of bacterial and viral diseases as well as complications related to such infections such as septic shock, adult respiratory distress and deterioration of cardiac function during endotoxin shock.

The effects of NAC are mediated directly and through the production of increased amounts of intracellular glutathione (Afaq F et al, "N-acetyl L-cysteine attenuates oxidant-mediated toxicity induced by chrysotile fibers," Toxicology Letters Vol. 117(1-2):53-60, Sep. 30, 2000). Many of the benefits seen in management of viral disease with NAC are mediated through free radical scavenging, particularly of the .OH radical. Removal of this radical performed by glutathione peroxidase, an enzyme that is mediated by the mineral selenium. The importance of selenium in supporting this reaction is demonstrated in a study that demonstrates that a non-lethal virus, Coxsackie virus, becomes lethal in animals deficient in selenium. It was determined that not only was the immune function of the animal altered, the viral genome was altered in such a way that the virus became more pathogenic (Beck M A, "Antioxidants and viral infections: host immune response and viral pathogenicity," Journal American College Nutrition, 20 (5 Suppl):384S-388S; discussion 396S-397S, October 2001). Selenium 100 mcg to 200 mcg should be given in addition to NAC to maintain and restore Selenium levels. Selenium may administered as organic forms of selenium, such as selenomethionine and selenocysteine, as well as the inorganic forms of the mineral, like sodium selenite and selenate.

Cell studies have demonstrated that a decreased level of glutathione increases sensitivity to radiation (Meister A et al, "Intracellular cysteine and glutathione delivery systems" Journal American College Nutrition 5(2):137-51, 1986). The ability of glutathione and its precursors to moderate the effect of the .OH radical makes NAC an ideal candidate for use in the treatment of radiation exposure. Scavengers of the .OH radical have been demonstrated to protect mammalian animal cells against the damaging effects of radiation (Ewing D et al, "Radiation protection of in vitro mammalian cells: effects of hydroxyl radical scavengers on the slopes and shoulders of survival curves," Radiation Res, Vol. 126(2):187-97, May 1991). The mechanism is related to the scavenging of the .OH radical as well as other intracellular mechanisms. An evaluation of 35 people with "post radiation syndrome" after exposure to substantial amounts of ionizing radiation (0.01-0.5 Gy) while participating in recovery work in Chernobyl demonstrated that they had a significant decrease in antioxidant defense with a decrease in the activity of glutathione peroxidase and deficiency of selenium (Kumerova A O et al, "Antioxidant defense and trace element imbalance in patients with postradiation syndrome: first report on phase I studies," Biology Trace Element Research Vol. 77(1):1-12, October 2000).

The "post radiation syndrome" produces headache, dizziness, poor memory, and local pains Id. These symptoms are not necessarily specific of any disease and may be easily confused with the early symptoms of illness such as viral influenza or even viral infection such as smallpox. The early symptoms of anthrax also mimic the early symptoms of viral influenza. Thus, it may be difficult to identify the etiologic cause of the early stage symptoms of biological weapons or radiation. The use of antioxidant support therapy with NAC is an inexpensive way to support an affected individual's antioxidant system while the specific etiology is identified and as an adjunct to antibiotic or antiviral therapy. The NAC antioxidant therapy may be initiated as either oral and/or intravenous therapy. Selenium should also be administered orally at 200 mg per day.

Additional factors also play a role in limiting the individual's ability to combat infection. The stress of infection with either microbial or viral agents will cause a shift in hormone production. This is manifest as a shift in the hypothalamo-pituitary-adrenal axis (HPA) with the resulting production of excess cortisol, the major glucocorticoid. Elevation in cortisol is accompanied by a decrease in cellular immunity in humans undergoing significant stress such as surgery (Tashiro T et al, "Changes in immune function following surgery for esophageal carcinoma," Nutrition, Vol. 15(10): 760-6, October 1999). Stress will also lower the response to vaccination and decrease protection to subsequent infection challenge in pigs immunized with a viral vaccine. Excess of the glucocorticoid is associated with suppression of antiviral immunity (Padgett D A et al, "Steroid hormone regulation of antiviral immunity," Ann N Y Acad Sci, Vol. 917:935-43, 2000). Counter regulation of immunosuppression due to glucocorticoid elevation would improve immune response and limit virus-mediated damage. Dehydroepiandrosterone (DHEA) and its metabolite Androstenediol (5-androstene-3 beta, 17 beta-diol, AED) have been demonstrated to be protective against lethal infection from Influenza A virus in animals Id. The effect is apparently due to a counterbalance of the immunosuppressive effect of glucorticoids. AED prevents the glucocorticoid-mediated suppression of IL-1, TNF-alpha and IL-2 secretion. An ocular infection model in mice exposed to herpes simplex virus 1 (HSV-1) was favorably modified by the subcutaneous administration of AED (Carr D J, J "Increased levels of IFN-gamma in the trigeminal ganglion correlate with protection against HSV-1-induced encephalitis following subcutaneous administration with androstenediol," Neuroimmunol Vol. 89(1-2):160-7, Aug. 14, 1998). The dose of AED used in this study was 320 mg/kg. The AED administration results in the increase of chemokines IP-10, MCP-1, the cytokine interleukin-6 (IL-6) and interferon-gamma (IFN-g) and IL-2 and natural killer cell activity, an important component of the removal of cells infected with virus. Thus, DHEA or AED becomes on an important component of antiviral therapy. Samuel et al, U.S. Pat. No. 6,168,804 refer to the use of DHEA as a component of a slow release vehicle to induce TH1 immune response to an immunizing antigen. Daynes et al, U.S. Pat. No. 5,919, 465, claim the use of DHEA to augment the immune response due to stress including the stress of viral infection. No patent, however, has claimed the use of a combination of NAC and DHEA or its metabolite AED as an immune enhancing combination for the treatment of viral diseases such as smallpox.

Vaccination after exposure to smallpox has been proposed as part of the management of the disease. Vaccination administered within 4 days of first exposure has been shown to offer some protection against acquiring infection and significant protection against a fatal outcome. (Henderson D A et al, "Consensus statement regarding Smallpox," Journal American Med Association June 9; 281(22):2127-37, 1999). As the presence of viral infection will decrease the level of glutathione it is likely that the immunization response may be compromised in individuals who are already carrying smallpox. It has been demonstrated that decreased immunologic function in individuals with cysteine or glutathione deficiency can be enhanced by cysteine supplementation (Dröge W et al, "Glutathione and immune function," Proc Nutrition Soc, Vol. 59(4):595-600, November 2000). Maintaining glutathione levels with glutathione precursors will improve the immune response to vaccination during vaccination for smallpox exposure. It is anticipated that inoculation for smallpox would be under taken at a time of concern about the appearance of smallpox used as a bioterror weapon. In this situation stress will be increased, and the use of the combination of NAC and DHEA is useful to maximize efficient immune response to immunization. The preferred method of use of the invention utilizes the combination of NAC and DHEA prior to or at the time of immunization.

OBJECTIVES OF THE INVENTION

The object of the invention is to generally deal with weapons of mass destruction exposure, particularly biological bioterror and radiation release (nuclear) weapons. Another object is to utilize systemic glutathione therapy with oral and intravenous NAC as well as intravenous and inhaled glutathione as a prophylactic, adjunct and frontline therapy in the treatment and support of individuals exposed to anthrax, small pox and radiation.

Another object is to utilize DHEA and systemic glutathione therapy as an adjunct and frontline therapy in the treatment and support of individuals exposed to small pox, viral disease and radiation.

Another object is to enable immediate treatment without fear of toxicity of individuals exposed to bioterror or radiation without fear of compromising later desired treatments, particularly in instances of delayed diagnosis.

Another object is to enable treatment of multiple vector exposure without fear of toxicity of individuals and without fear of compromising later desired treatments, particularly useful where a number of threats may be combined.

Another object is that in the event of mass attack, not everyone will be exposed or present with symptoms, and this invention, utilizing NAC, enables some treatment by purchasing economically in relatively vast quantities enabling more optimal use of more limited and considerably more expensive antibiotic, anti-viral and vaccination resources.

For patients who present with ambiguous symptoms for whom antibiotic treatment may be premature or have severe side effects, or patients with risk of exposure to anthrax but demonstrating no symptoms, the invention proposes an immediate method to blunt any toxin effects while awaiting testing.

For patients who present with symptoms suggesting the need for antibiotic therapy, the invention enables the individual to begin immediate toxin management. The antibiotic is designed to slow and eliminate the reproduction of anthrax spores, but the antibiotic is ineffective for toxin detoxification.

For patients with compromised immune systems, either from anthrax or other cause such as HIV or other disease, the invention accomplishes immune system enhancement, and detoxification of anthrax toxin while the antibiotic takes effect.

For patients with inhalation anthrax, for whom the prognosis is very poor, the addition of IV NAC offers one of the few non-toxic detoxification regimes to interrupt the dramatic and life-threatening effect of toxin release and apoptotic effect triggered by *Bacillus anthracis*.

The invention also can give partial protection against changes by bioterrorists to the anthrax activity because the invention combats through natural metabolic pathways the toxin effect whatever the strain of anthrax that is the source. Such sources may change because of the emergence of antibiotic resistant strains either through natural selection or the introduction of antibiotic resistance through genetic manipulation by manufacturers of bioterror weapons.

DESCRIPTION OF INVENTION

Pharmacologic Compounds

NAC will be the collective reference for glutathione pathway enhancing compounds in this description. Those compounds include N-acetyl-cysteine which is normally referred to as NAC, but in this invention, the term NAC, and the term glutathione precursor, also includes the following:

Cystine is (3,3'-dithiobis [2-aminopropanoic acid]). Cystine is readily reduced to cysteine. Cystine is present in most mammalian hair and keratin.

Cysteine is 2-amino-3-mercapto propanoic acid. It is readily converted by oxidoreduction to cystine. It is a constituent of glutathione and abundantly present in the metallothioneines.

Cystine in the body-useful form as L-cystine is available from Spectrum Chemical Mfg. Corp. 14422 S. San Pedro St., Gardena, Calif. 90248.

Cystine, cysteine, and N-Acetyl cysteine and pharmaceutically acceptable salts, including the pharmaceutically active forms described in Kozhemyakin et al, published by WIPO as WO 00/031120, PCT/RU99/00453, filed internationally on 19 Nov. 1999, "Hexapeptide with the Stabilized Disulfide Bond and Derivatives Thereof Regulating Metabolism, Proliferation, Differentiation and Apoptosis,"-will all collectively be referred to as NAC in this invention. Other glutathione pathway enhancing compounds understandable to one of ordinary skill in the art which are encompassed in the term NAC are stable forms of compounds that enhance the glutathione pathway, the substituents of which are suggested in Kozhemyakin et al, Hexapeptide with the Stabilized Disulfide Bond and Derivatives thereof. Regulating Metabolism, Proliferation, Differentiation and Apoptosis published as WO 00/31120, Jun. 2, 2000. Included in the term NAC is also any therapeutically beneficial sulfur-donating compound, such as lipoic acid and including ebselen and s-acetyl-glutathione, which interacts with the glutathione pathway and the monoethyl ester of glutathione (in which the glycine carboxyl group is esterified) (Puri R N, Meister A. "Transport of glutathione, as gamma-glutamylcysteinylglycyl ester, into liver and kidney", Proc National Academy Science USA, Vol. 80(17):5258-60, September 1983). The invention contemplates in the term NAC undenatured whey protein products designed to have enhanced cystine concentration as well as protein products that contain cysteine and cystine. They can be in the form of food products.

The addition of cystine, cysteine, N-acetyl cysteine, or the pharmaceutically acceptable salt of those substances yields another effect in this invention not facially evident from the independent properties of the basic components of the invention (hereafter each substance or a pharmaceutically acceptable salt is referred to as a "cystine"). Administration of a cystine family member, preferably cystine, which has the best and most rapid upload into the glutathione pathway and better storage capability by the body, or N-acetyl cysteine, enhances the immune system competency of the patient.

In individuals on prophylactic therapy including antiviral agents for presumed exposure to smallpox or potassium iodide for radiation the NAC can be continued for extended periods with oral ingestion of NAC or a cystine source such as undenatured whey protein such as Immunocal (a Registered Trademark of a product manufactured by Immunotec, Montreal Canada). Immunocal® undenatured whey protein has the added advantage of providing the cysteine in the disulfide form, called cystine. 80% of the circulating cysteine in the body is in the form of cystine. Cystine is readily absorbed into cells and has been demonstrated to be preferred by certain cells such as astrocytes (Kranich O et al, "Utilization of cysteine and cysteine precursors for the synthesis of glutathione in astroglial cultures: preference for cystine," Glia. Vol. 22(1):11-8 Jan. 1998.).

The NAC may be used in combination with anthrax vaccine to minimize side effects, or as an alternative for those intolerant of anthrax vaccine pending presentment with symptoms.

The reference to anthrax antibiotic or "antibiotic" is to antibiotics for combating anthrax or other bacterial diseases that are effective bioterror agents which are listed below.

Antibiotics that have been accepted for use in the treatment of anthrax include Penicillin, Doxycycline and Ciprofloxacin.

The present invention may be combined with other antibiotics as well.

These antibiotics would include, but not be limited to

1. Aminoglycoside=Gentamicin, Tobramycin, Netilmicin, Amikacin, Streptomycin.
2. Cephalosporins=Cefazolin, Cefuroxiine, Cefotetan, Ceftriaxone, Ceftazidine.

3. Clindamycin
4. Macrolides=Erythromycin, Clarithromycin, Azithromycin.
5. Metronidazole
6. Penicillins=Penicillin, Ampicillin, Nafcillin, Piperacillin. With or without Aztreonam, Imipenem, or with Beta-lactamase inhibitor=Ampicillin/sulbactam (Augmentum) or Pipercillin/tazobactam and Beta-lactam=Ceftriaxone, Cefuroxime
7. Quinolones=Ciprofloxacin, Ofloxacin, Gatifloxacin or Trovafloxacin
8. Tetracyclines=Tetracycline, Doxycycline, or Minocycline
9. Trimethoprim-Sulfamethoxazole
10. Vancomycin
11. Chloramphenicol
12. Erythromycin Antibiotic dosing schedule per Hanna P, "Medical Review of anthrax," The New England Journal of Medicine Volume 341(11);815-825, 1999 PHARMACOLOGIC THERAPY FOR BACILLUS ANTHRACIS INFECTION AND ITS SEQUELAE.

| Treatment of infection | | |
|---|---|---|
| Therapy | Dosage for Adults | Dosage for children |
| Penicillin V | 200-500 mg orally 4 times/day | 2550 mg/kg of body weight/day orally in divided doses 2 or 4 times/day |
| Penicillin G | 8 million-12million U total, intravenously in divided doses every 46 hr | 100,000-150,000 U/kg/day in divided doses |
| Streptomycin | 30 mg/kg intramuscularly or intravenously per day - gentamicin can also be used (in conjunction with penicillin) | |
| Tetracycline | 250-500 mg orally or intravenously 4 times/day | Tetracycline is not approved for children |
| Doxycycline | 200 mg orally or intravenously as a loading dose, then 50100 mg every 12 hr | Doxycycline is not approved for children <9 yr old For children <<45 kg: 2.5 mg/kg every 12 hr For children >45 kg: use adult dosage |
| Erythromycin | 250 mg orally every 6 hr | 40/mg/kg/day orally in divided doses every 6 hr |
| Erythromycin lactobionate | 1520 mg/kg (maximum, 4 g) intravenously per day | 20-40 mg/kg/day intravenously in divided doses every 6 hr (1- to 2-hr infusion) |
| Chloramphenicol | 50-100 mg/kg/day orally or intravenously in divided doses every 6 hr | 50-75 mg/kg/day in divided doses every 6 hr |
| Ciprofloxacin | 250-750 mg orally twice/day 200-400 mg intravenously every 12 hr | 20-30 mg/kg/day in divided doses every 12 hr Oral or intravenous dosing is not approved for patients <18 yr old |

| Prophylaxis | | |
|---|---|---|
| Antibiotic | Adult dosage | Child Dosage |
| Doxycycline | 100 mg orally twice/day for 4 wk | |
| Ciprofloxacin | 500 mg orally twice/day for 4 wk | |

| Corticosteroid therapy for severe edema | | |
|---|---|---|
| Dexamethasone | 0.750.90 mg/kg/day orally, intravenously, or intramuscularly in divided doses every 6 hr | 0.25-0.5 mg/kg every 6 hr |
| Prednisone | 12 mg/kg or 560 mg orally/day | 0.52 mg/kg/day |

Most *B. anthracis* strains are resistant to cefuroxime in vitro.

For inhalational, gastrointestinal, or meningeal anthrax infection in adults, the intravenous regimen is used with penicillin G, streptomycin, tetracycline, doxycycline, erythromycin lactobionate, chloramphenicol, and ciprofloxacin; for these infections in children, the intravenous regimen is used with penicillin G, doxycycline, erythromycin lactobionate, and chloramphenicol.

Selenium will be the collective reference for selenium enhancing compounds in this description. Those compounds include Selenium which is normally referred to as Selenium, but in this invention, the term selenium, also includes the following: Selenium may administered as organic forms of selenium, such as selenomethionine and selenocysteine, as well as the inorganic forms of the mineral, like sodium selenite and selenate.

If patient is unvaccinated, initial doses of vaccine may be begun.

FURTHER INFORMATION ON THE INVENTION

While infection with *Bacillus anthracis* in the past has been generally treated with only antibiotic therapy there are other compelling reasons to consider adjunctive therapy of NAC. The reasons include the emergence of antibiotic resistant strains either through natural selection or the introduction of antibiotic resistance through genetic manipulation by manufacturers of bioterror weapons. Another factor is the observation that even with antibiotic therapy the bacteria may have the opportunity to manufacture sufficient quantity of toxin to compromise the individual. Antibiotic therapy does not address the effect of the toxin on the immune system. (Hanna Pet al, "Role of macrophage oxidative burst in the action of anthrax lethal toxin," Mol Med 1994 November; 1(1):7-18.

The present invention discloses the use of specific antioxidants delivered as systemic infusions or via inhalation therapies. The effectiveness of the therapy can be enhanced using blood sample monitoring of glutathione levels. Glutathione can be measured in the serum, white blood cell or red blood cell. There is no risk to elevating the level of the precursors of glutathione such as NAC as gamma-glutamylcysteine the direct precursor of glutathione is regulated by the enzyme glutamyl synthase. The feedback regulator of glutathione production in the cell is the level of glutathione. If glutathione is low and glutathione precursors are available, the cell mechanisms will form glutathione. If adequate glutathione is present, additional glutathione is not produced. Cysteine or cystine has been shown to be the rate limiting factor in the production of glutathione (Meister, "New aspects of glutathione biochemistry and transport-selective alteration of glutathione metabolism," Nutrit Rev 1984; 42:397-410). Monitoring the level of glutathione will maximize the dosing schedule for the glutathione precursor being used.

Intravenous NAC is normally not recommended as a stand-alone therapy, but as a preliminary non-toxic therapy in patients presenting with no symptoms or ambiguous symptoms, or for particularly sensitive individuals such as pregnant women or children for whom premature and ultimately unnecessary treatment for symptoms determined to be unrelated to anthrax could have undesired side effects. The preferred mode is envisioned to be used in combination with appropriate antibiotics. Antibiotics that have been accepted for use in the treatment of anthrax include Penicillin, Doxycycline and Ciprofloxacin. The addition of an adjunctive therapy to delay the effect of the anthrax toxin is useful even with early and vigorous treatment, the prognosis of inhalation, gastrointestinal or meningeal anthrax remains poor (Hanna P, "Medical Review of anthrax," The New England Journal of Medicine Volume 341(11);815-825, 1999).

In defense against Biological Terror weapons, the invention would also be useful for use as an initial therapeutic for individuals who may have been exposed to a presumed toxin, and while confirmation and identification of exposure is pending. In other words, IV antioxidant such as NAC or glutathione will attenuate the impact of the anthrax toxin; reducing the likelihood of severe impact from the toxin and act as an attenuator of the toxin while confirmation of exposure is pending. The effect of NAC on the immune system would be beneficial even if the biological turned out to be something other than anthrax as the improved immune function would be useful in defending the individual against viruses (De Flora S, et al, "Attenuation of influenza-like symptomatology and improvement of cell-mediated immunity with long-term N-acetylcysteine treatment," Eur Respir J 1997 July; 10(7):1535-41).

This is a reasonably priced therapy with fewer side effects for persons presenting with modest or ambiguous symptoms and who are awaiting anthrax culture results.

Positive anthrax culture results justify aggressive intervention with both antibiotic and antioxidant therapy because of the severity of the infection and the lack of side effects from the systemic antioxidant therapy. That aggressive intervention requires both interference with toxin effects achieved by NAC or its pharmaceutical equivalent referenced in this invention, and antibiotic treatment.

The NAC may be used in combination with smallpox vaccine to minimize side effects, or as an alternative for those in tolerant of smallpox vaccine pending presentment with symptoms or as an adjunct in patients undergoing prophylactic smallpox immunization. It may also be used as a prophylactic for individuals concerned about possible exposure to radiation.

At the present time no antiviral drug has been demonstrated to be effective against smallpox. Due to the communicability of smallpox, animal studies have not been performed using available antiviral medications. However, there are suggestions that at least one of the currently available antiviral drugs may be useful (Haney D, Associated press Nov. 21, 2001 http://ap.tbo.com/ap/breaking/MGAVLPA2AUC.html). The most promising drug is cidofovir, an intravenous medication used in the treatment of cytomegalovirus. While oral or intravenous NAC therapy may be initiated prior to considering antiviral medications, the preferred mode is envisioned to be used in combination with appropriate antiviral medications. These may include, in addition to cidofivar, Broad spectrum antivirals such as the Triazole carboxamine Ribavirin, protease inhibitors such as Saquinavir, Ritonavir, Indinavir, and Nelfinavir. Compatible antivirals also include the tricyclic amines such as Amantadine and Rimantadine as well as the Meuraminic acid mimetics such as Relenza and Tamiflu, and the small cyclics such as Pleconaril. Additional antiviral medications include Nucleoside analogues such as Vidarabine, Acyclovir, Gancyclovir, valganciclovir, Nucleoside Reverse transcriptase inhibitors such as Zidovudine (AZT), Didanosine (ddI), Zaocaitabine (ddC), Stravudine (d4T), Lamivudine (3TC) and Non-Nucleoside Reverse transcriptase inhibitors such as Nevirapine, and Delaviridine.

The present invention discloses the use of specific antioxidants delivered as oral therapies, systemic infusions or via inhalation therapies. The effectiveness of the therapy can be enhanced using blood sample monitoring of glutathione levels. Glutathione can be measured in the serum, white blood cell or red blood cell. There is no risk to elevating the level of the precursors of glutathione such as NAC as gamma-glutamylcysteine the direct precursor of glutathione is regulated by the enzyme gamma-glutamyl synthase. The feedback regulator of glutathione production in the cell is the level of glutathione. If glutathione is low and glutathione precursors are available, the cell mechanisms will form glutathione. If adequate glutathione is present, additional glutathione is not produced. Cysteine or cystine has been shown to be the rate-limiting factor in the production of glutathione (Meister A, "New aspects of glutathione biochemistry and transport-selective alteration of glutathione metabolism," Nutrit Rev 1984; 42:397-410). Monitoring the level of glutathione will maximize the dosing schedule for the glutathione precursor being used.

Oral or intravenous NAC is normally not recommended as a stand-alone therapy, but as a preliminary non-toxic therapy in patients presenting with no symptoms or ambiguous symptoms, or for particularly sensitive individuals such as pregnant women or children for whom premature and ultimately unnecessary treatment for symptoms determined to be unrelated to smallpox could have undesired side effects. While the preferred mode is in combination with a specific antiviral therapy there is no current consensus that antiviral therapy would be effective. For individuals intending to be immunized against smallpox it is useful to begin oral NAC prior to the immunization. In the preferred mode the individual would begin oral NAC at least two days prior to the immunization. The use of NAC to maximize the effectiveness of immunization may begin 2 weeks prior to immunization in situations in which the vaccination is elective. The earlier use of NAC will also help diminish side effects from the administration of the vaccination.

In defense against Biological Terror weapons one of the greatest problems is the anxiety created when presumed exposures occur. It may be difficult to determine if the exposure has been bacterial, viral, radiation or a combination of these materials. The invention would also be useful for use as an initial therapeutic for individuals who may have been exposed smallpox or other toxin, and while confirmation and identification of exposure is pending. In other words, antioxidant such as NAC, oral or IV, or IV glutathione will attenuate the impact of the smallpox virus or the severity of the infection, reducing the likelihood of severe impact from the exposure and act as an attenuator of the virus while confirmation of exposure is pending. The effect of NAC on the immune system would be beneficial even if the biological weapon turned out to be something other than smallpox or radiation as the improved immune function would be useful in defending the individual against viruses in general and enhances the antioxidant capacity of the body (De Flora S, et al, Attenuation of influenza-like symptomatology and improvement of cell-mediated immunity with long-term N-acetylcysteine treatment, Eur Respir Jour Vol. 10(7):1535-41 Jul. 1997. The reduction in anxiety facilitated by being able to initiate a therapy with minimal side effects that enhances immune function as well as well reduces the impact of toxins and radiation may be very beneficial to the health of individuals as well as the general population. This is a reasonably priced therapy with few if any side effects for persons presenting with modest or ambiguous symptoms and who are awaiting confirmation of exposure or definitive culture.

Positive identification of infection with smallpox justifies aggressive intervention with antioxidant therapy because of the severity of the infection and the lack of side effects from the systemic antioxidant therapy. In the treatment of small pox additional therapy with antiviral medication and antibiotic for specific complications is warranted and will be enhanced by the use of systemic antioxidant therapy achieved by oral or intravenous NAC or its pharmaceutical equivalent referenced in this invention.

The invention may be packaged in the form of powdered NAC either by itself or in combination with Selenium and/or DHEA for convenience of use. This would be particularly advantageous to individuals engaged in activities that require them to pack their supplies such as soldiers in the field. The example of soldiers typifies the situation in which availability of the invention for prophylaxis, early treatment or aggressive treatment of exposure to bioterror weapons is important. The invention may be prepackaged with antibiotic and/or antiviral therapy to facilitate rapid, easy use. Like wise the invention may be incorporated into a food product using cold mixing techniques.

The use of laboratory assessment of the glutathione levels and antioxidant capacity is useful in order to maximize the therapy.

Assessment of the glutathione levels and antioxidant capacity also defines a second population at risk for greater susceptibility to infection as well as complications from smallpox infection. Smallpox infection in unvaccinated populations has a reported mortality rate of 30%. Large-scale studies have not been done, but it is likely that populations deficient in glutathione and overall antioxidant capacity are at greater risk due to their inability to mount an adequate TH1 and NK cell response. The use of baseline assessment of glutathione level and antioxidant capacity early after concern of exposure will identify individuals who may be at greater risk of progressing with smallpox after exposure or of greater risk of complication. The use of NAC immediately prior to at the time of immunization for smallpox will also lessen the likelihood of developing a complication of the vaccination. As the vaccine is composed of a live, less virulent form of "pox" virus there is a risk estimated to be as high as 1:100,000 of developing serious side-effects including encephalitis. The CDC estimates the fatality rate of smallpox vaccination encephalitis to be as high as 50% (http://www.bt.cdc.gov/agent/smallpox/vaccination/facts.asp).

Dosing

Selenium should also be administered 200 mg per day.

NAC IV infusion, 150 mg/Kg in 250 ml of D5W over 15 minutes

Followed by continuous infusion of 50 mg/kg in 500 ml over 4 hr

Has been demonstrated to be safe and effective in a small study (Spapen H et al, "Does N-acetyl-L-cysteine influence cytokine response during early human septic shock?," Chest, 113(6):1616-24 1998 June). The intravenous infusion could be continued to for as long as needed depending on the individual's response to the therapy.

Intravenous NAC is not normally recommended as a standalone therapy, but is envisioned to be used in combination with antibiotics when necessary. It would also be useful for use as an initial therapeutic for individuals who may have been exposed, and while confirmation of exposure is pending. In other words, an oral or short IV dose will potentially attenuate the impact of the anthrax, smallpox virus or radiation, reducing the likelihood of severe infection from the biologic agent and acts as a preventative while confirmation of exposure is pending. The effect of NAC on the immune system would be beneficial even if the biological turned out to be something other than smallpox as the improved immune function would be useful in defending the individual against viruses (De Flora S, et al, Eur Respir J. Vol. 10(7):1535-41 July 1997.

Intravenous NAC is manufactured using pharmaceutical grade NAC obtained from any major supplier of USP grade NAC, such as Spectrum Chemical Mfg. Corp. 14422 S. San Pedro St., Gardena, Calif. 90248. 8 grams of NAC are diluted in 100 ml sterile water or saline for injection. The process is performed using a layer of nitrogen gas to expel the excess oxygen overlying the liquid. This step is done to maintain an oxygen free environment that will limit the amount of oxidation that may occur during storage.

Oral dosage of NAC for prophylaxis is 500 mg. two or three times a day.

Oral dosage for use prior to immunization is 500 mg. two to three a day beginning two days prior to immunization. If it is not possible to initiate NAC prior to immunization initiation of NAC at the time of immunization is acceptable.

Intravenous glutathione is prepared in a similar fashion using reduced L-glutathione obtained from any major supplier of USP grade NAC, such as Spectrum Chemical, Gardena, Calif. The glutathione is diluted in sterile water or saline using 200 mg glutathione per ml of diluent. Doses range is 400-1200 mg per day.

Glutathione may also be administered by inhalation with the use of a nebulizer. The reduced form of L-glutathione can be mixed in sterile saline in concentrations of 60 mg/ml, or 100 mg/ml and administered as 2 ml to 4 times per day. The frequency of administration will depend on the severity of the patient's condition.

Inhaled glutathione 60 mg/ml may be mixed with NAC at a dose of 125 mg/ml, and administered at a dose of 2 ml 2 to 4 times a day.

DHEA in a dose sufficient to obtain the desired clinical effect. Dosing may range from 50 ing per day for 5 days to 300 mg/kg per day for 5 days.

Dosage for use for prophylaxis in adults if smallpox exposure possible in the future and for use after routine preventative vaccination with vaccinia: NAC 1000 mg per day in two divided doses. This should be used on a continuous basis. Children should use a dose of NAC equivalent to 14 mg/Kg of body weight daily in divided doses. If using a whey protein concentrate such as Immunocal the dose for Adults is 10 grams of whey protein a day for children ½ pack per day.

Dosage for use after small pox exposure with or without vaccination: Adults—NAC 2000 mg per day in two or four divided doses. Children—14-20 mg/Kg body weight daily in divided doses.

Doses for use for prophylaxis of exposure to radiation:

Adults—NAC 1000 mg per day in two divided doses. This should be used on a continuous basis. Children—should use a dose of NAC equivalent to 14 mg/Kg of body weight daily in divided doses. If using a whey protein concentrate such as Immunocal the dose for Adults is 20 grams of whey protein a day for children ½ to 1 pack per day. These doses should be continued for the duration of the exposure and for 2 to 4 weeks after the exposure. If the exposure is high dose radiation, the dosage should be continued for 6 months.

Dosage for use if anthrax or smallpox infection is likely or effects of infection are suspected: Use the doses recommended for exposure to smallpox combined with the use of intravenous NAC: loading is 150 mg/kg in 250 ml of D5W, over 15 minutes. This was followed by continuous infusion of 50 mg/kg in 500 ml over 4 hrs. In a 70 kg man this translates to 10.5 grams (10,500 mg) over 15 minutes. This dose is then followed by 3500 mg (3.5 gms) over 4 hours. The total is 14 gms in 4 hours. The patient may be continued on oral NAC using the dosage for post exposure. This dose may be supplemented with inhaled glutathione 60 mg/ml, 2 ml 2 to 4 times a day. Additionally Intravenous glutathione may be used particularly if there are signs of central nervous system involvement using a dose of 600 mg twice a day. The addition of DHEA with Dosing ranges from 50 mg per day for 5 days to 300 mg/kg per day for 5 days is recommended.

Doses for use for prophylaxis of exposure to radiation: NAC 1000 mg per day in two divided doses. This should be used on a continuous basis. Children should use a dose of NAC equivalent to 14 mg/Kg of body weight daily in divided doses. If using a whey protein concentrate such as Immunocal the dose for Adults is 20 grams of whey protein a day for children ½ to 1 pack per day.

Dosage for use after radiation exposure: Adults—NAC 2000 to 4000 mg per day in two or four divided doses. Children—14-20 mg/Kg body weight daily in divided doses. If using a whey protein concentrate such as Immunocal the dose for Adults is 20-30 grams of whey protein a day for children ½ to 1 pack per day. The addition of DHEA with Dosing ranges from 50 mg per day for 5 days to 300 mg/kg per day for 5 days is recommended.

If symptoms of radiation toxicity are developing Use the doses recommended for exposure to radiation combined with the use of intravenous NAC: loading is 150 mg/kg in 250 ml of D5W, over 15 minutes. This was followed by continuous infusion of 50 mg/kg in 500 ml over 4 hrs. In a 70 kg man this translates to 10.5 grams (10,500 mg) over 0.15 minutes. This dose is then followed by 3500 mg (3.5 gms) over 4 hours. The total is 14 gms in 4 hours. The patient may be continued on oral NAC using the dosage for post exposure.

This dose may be supplemented with inhaled glutathione 60 mg/ml, 2 ml 2 to 4 times a day. Additionally Intravenous glutathione may be used particularly if there are signs of central nervous system involvement using a dose of 600 mg twice a day. The addition of DHEA with Dosing ranges from 50 mg per day for 5 days to 300 mg/kg per day for 5 days is recommended.

Dosage for use if effects of infection related to Biological terror weapon other than anthrax or smallpox, such as another virus are suspected: Use the doses recommended for exposure to smallpox combined with the use of intravenous NAC: loading is 150 mg/kg in 250 ml of D5W, over 15 minutes. This was followed by continuous infusion of 50 mg/kg in 500 ml over 4 hrs. In a 70 kg man this translates to 10.5 grams (10,500 mg) over 15 minutes. This dose is then followed by 3500 mg (15 gms) over 4 hours. The total is 14 gms in 4 hours. The patient may be continued on oral NAC using the dosage for post exposure.

This dose may be supplemented with inhaled glutathione 60 mg/ml, 2 ml 2 to 4 times a day. Additionally Intravenous glutathione may be used particularly if there are signs of central nervous system involvement using a dose of 600 mg twice a day. The addition of DHEA with Dosing ranges from 50 mg per day for 5 days to 300 mg/kg per day for 5 days is recommended.

Management Information:

Intravenous NAC has a small risk as noted in a small group of patients given IV NAC. Rare episodes of "anaphylactoid" reaction manageable with benedryl have been reported (Bailey B et al Ann Emerg Med, 31(6):710-51998). It has been observed that NAC infusion may be restarted shortly after initiating benedryl without risk. "Non-life-threatening anaphylactoid reactions to intravenous NAC are treated easily and the infusion may be continued or restarted safely after the administration of diphenhydramine" (Bailey B et al, Ann Emerg Med, 31(6):710-51998). Intravenous glutathione will have no greater incidence of reaction than intravenous NAC. While administering intravenous glutathione in numerous cases, no episodes of reactions have been observed by the inventors.

An excess of glutathione (GSH) does not appear practically possible with the use of NAC. The formation of GSH inside of cells is regulated by a feedback mechanism that prevents excess formation as the level of glutathione regulates the formation of additional glutathione. Thus, there is no concern that an excess of glutathione will be formed. As the glutathione is depleted, additional glutathione is formed. In deficient states, the availability of the amino acid cysteine becomes the rate-limiting factor in the synthesis of GSH (Meister A, "New aspects of glutathione biochemistry and transport-selective alteration of glutathione metabolism," Nutrit Rev Vol. 42:397-410, 1984.). Oral glutathione has not been demonstrated to increase the level of glutathione in the White Blood Cells (Meister A, "New aspects of glutathione biochemistry and transport-selective alteration of glutathione metabolism," Nutrit Rev Vol. 42:397-410, 1984.). Thus, it was initially conjectured that intravenous glutathione would have little beneficial effect. The observation of reduction in the severity of tremor in patients with Parkinson's disease strongly suggests that IV glutathione transits the blood brain barrier and is absorbed into cells (Such G, "Reduced glutathione in the treatment of early Parkinson's disease" Neuropsychopharmacology Biology Psychology October, 1996). This feature of the invention will help reduce the incidence of meningitis associated with viral infection such as small pox.

The invention also refers to not only combinations, but also methods of treatment, including serial or combined doses of the substances suggested above, and methods of manufacturing them in tandem. The intent is to administer therapeutic doses of the substances referred to herein. The term "therapeutic dose" is intended to mean that amount of a drug or pharmaceutical agent that will elicit the biological or medical response of a tissue, a system, animal or human that is being sought by a researcher, veterinarian, medical doctor or other clinician. The term "prophylactically effective amount" is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. A consideration of these factors is well within the purview of the ordinarily skilled clinician for the purpose of determining the therapeutically effective or prophylactically effective amount. "Therapeutic window" is the therapeutic dose between the minimum amount of and the maximum amount of a pharmaceutical drug that will prevent or reduce the risk of occurrence of the biological or medical event that is sought to be prevented in a tissue, a system, animal or human by a researcher, veterinarian, medical doctor or other clinician. A "prophylactic dose" dose contemplates a dose that may be slightly less than the normal minimum amount of a pharmaceutical drug that will treat a biological or medical event that is sought to be overcome in a tissue, a system, animal or human by a researcher, veterinarian, medical doctor or other clinician, and addresses the problem of minimizing the toxicity of many drugs while having at least some of the drug present in the mammalian system to reduce the time before effective treatment by a drug begins.

The invention is not meant to be limited to the disclosures, including best mode of invention herein, and contemplates all equivalents to the invention and similar embodiments to the invention for humans and mammals and veterinary science. Equivalents include all pharmacologically active racemic mixtures, diastereomers and enantiomers of the listed compounds and their pharmacologically acceptable salts in any pharmaceutically acceptable carrier.

What is claimed is:

1. A method of ameliorating the effects of exposure to small pox as a viral bioterror weapon comprising the following steps:
    administering to a person in a pharmaceutically acceptable carrier at least one therapeutic dose of NAC; and
    administering at least one therapeutic dose of at least one antiviral agent to said small pox as the viral bioterror weapon.

2. The method according to claim 1, further comprising the additional step:
    administering a therapeutic dose of selenium.

3. The method according to claim 2, further comprising the additional step:
    administering a therapeutic dose of dehydroepiandrosterone.

* * * * *